United States Patent
Blus et al.

(10) Patent No.: US 10,325,736 B2
(45) Date of Patent: Jun. 18, 2019

(54) DEVICE WITH MOVABLE BUTTONS OR SWITCHES

(71) Applicant: GYRUS ACMI, INC., Southborough, MA (US)

(72) Inventors: Theodore Blus, Shoreview, MN (US); Riyad Moe, Madison, WI (US)

(73) Assignee: GYRUS ACMI, INC., Southborough, MA (US)

( * ) Notice: Subject to any disclaimer, the term of this patent is extended or adjusted under 35 U.S.C. 154(b) by 42 days.

(21) Appl. No.: 15/657,904

(22) Filed: Jul. 24, 2017

(65) Prior Publication Data
US 2017/0323744 A1 Nov. 9, 2017

Related U.S. Application Data

(63) Continuation of application No. 14/987,233, filed on Jan. 4, 2016, now Pat. No. 9,748,057.

(51) Int. Cl.
*H01H 9/26* (2006.01)
*H01H 13/70* (2006.01)
(Continued)

(52) U.S. Cl.
CPC ......... *H01H 13/70* (2013.01); *A61B 18/1442* (2013.01); *H01H 9/26* (2013.01);
(Continued)

(58) Field of Classification Search
CPC .............. H01H 1/12; H01H 1/18; H01H 1/22; H01H 1/36; H01H 3/02; H01H 3/00; H01H 3/12; H01H 5/00; H01H 5/04; H01H 13/00; H01H 13/22; H01H 13/26; H01H 13/50; H01H 13/52; H01H 2003/12;
(Continued)

(56) References Cited

U.S. PATENT DOCUMENTS

| | | |
|---|---|---|
| 4,181,826 A | 1/1980 | Latasiewicz |
| 4,256,931 A | 3/1981 | Palisek |

(Continued)

FOREIGN PATENT DOCUMENTS

| | | |
|---|---|---|
| EP | 1852078 A1 | 11/2007 |
| EP | 1897506 A1 | 3/2008 |

OTHER PUBLICATIONS

International Search Report and Written Opinion from the European Patent Office for Application No. PCT/US2016/067956, dated Mar. 24, 2017.

*Primary Examiner* — Anthony R Jimenez
(74) *Attorney, Agent, or Firm* — The Dobrusin Law Firm, P.C.; Joseph L. Kallie

(57) ABSTRACT

A surgical device comprising: (a) one or more functional elements, and (b) a selector assembly including: (i) one or more activation buttons, (ii) one or more circuit board switches, and (iii) a shuttle in communication with the circuit board switches or the one or more activation buttons to move the circuit board switches or the activation buttons between at least a first position and a second position so that the circuit board switches or the activation buttons are moveable relative to each other; wherein the one or more functional elements provide a first function when the circuit board switches or the one or more activation buttons are in the first position, and the one or more functional elements provide a second function when the circuit board switches or the one or more activation buttons are in the second position.

19 Claims, 7 Drawing Sheets

(51) Int. Cl.
  *A61B 18/14* (2006.01)
  *A61B 18/00* (2006.01)
  *A61B 17/00* (2006.01)

(52) U.S. Cl.
  CPC . *A61B 18/1402* (2013.01); *A61B 2017/00376* (2013.01); *A61B 2018/00607* (2013.01); *A61B 2018/00922* (2013.01); *A61B 2018/00946* (2013.01); *A61B 2018/00958* (2013.01); *A61B 2018/00994* (2013.01); *A61B 2018/1455* (2013.01); *H01H 2231/048* (2013.01)

(58) Field of Classification Search
  CPC ........... H01H 2003/32; H01H 2215/00; H01H 2215/004; H01H 2221/00; H01H 2221/014; H01H 25/008; H01H 9/02; H01H 13/14; H01H 13/70; H01H 9/26; A61B 2017/00376; A61B 2018/00607; A61B 2018/00922; A61B 2018/00946; A61B 2018/00958; A61B 2018/00994; A61B 2018/1455
  USPC ................................................ 200/573, 5 A
  See application file for complete search history.

(56) References Cited

U.S. PATENT DOCUMENTS

| | | | |
|---|---|---|---|
| 4,319,099 | A | 3/1982 | Asher |
| 4,504,707 | A | 3/1985 | Ochiai |
| 4,703,139 | A | 10/1987 | Dunlap |
| 4,802,476 | A | 2/1989 | Noerenberg et al. |
| 4,846,516 | A | 7/1989 | Yuh et al. |
| 5,035,695 | A | 7/1991 | Weber, Jr. et al. |
| 5,071,426 | A | 12/1991 | Dolgin et al. |
| 5,226,904 | A | 7/1993 | Gentelia et al. |
| 5,376,765 | A | 12/1994 | Holmes et al. |
| 5,399,823 | A | 3/1995 | McCusker |
| 5,472,442 | A | 12/1995 | Klicek |
| 5,743,384 | A | 4/1998 | Clark |
| 6,110,171 | A | 8/2000 | Rydell |
| 6,113,596 | A | 9/2000 | Hooven et al. |
| 6,190,386 | B1 | 2/2001 | Rydell |
| 6,310,308 | B1 | 10/2001 | Watson et al. |
| 6,358,268 | B1 | 3/2002 | Hunt et al. |
| 6,423,918 | B1 | 7/2002 | King et al. |
| 6,551,313 | B1 | 4/2003 | Levin |
| 6,679,882 | B1 | 1/2004 | Kornerup |
| 7,232,440 | B2 | 6/2007 | Dumbauld et al. |
| 7,687,734 | B2 | 3/2010 | Weber |
| 7,902,474 | B2 | 3/2011 | Mittleman et al. |
| 8,089,017 | B2 | 1/2012 | Chen et al. |
| 8,262,655 | B2 | 9/2012 | Ghabrial et al. |
| 8,378,240 | B2 | 2/2013 | Rajagopal et al. |
| 2005/0113827 | A1 | 5/2005 | Dumbauld et al. |
| 2005/0130697 | A1 | 6/2005 | Dyer |
| 2005/0187512 | A1 | 8/2005 | Isola et al. |
| 2006/0084973 | A1 | 4/2006 | Hushka |
| 2011/0220479 | A1 | 9/2011 | Zhou |
| 2012/0123405 | A1 | 5/2012 | Moua et al. |
| 2014/0048397 | A1 | 2/2014 | Sykes et al. |
| 2014/0276795 | A1 | 9/2014 | Batchelor et al. |
| 2014/0276799 | A1 | 9/2014 | Batchelor et al. |

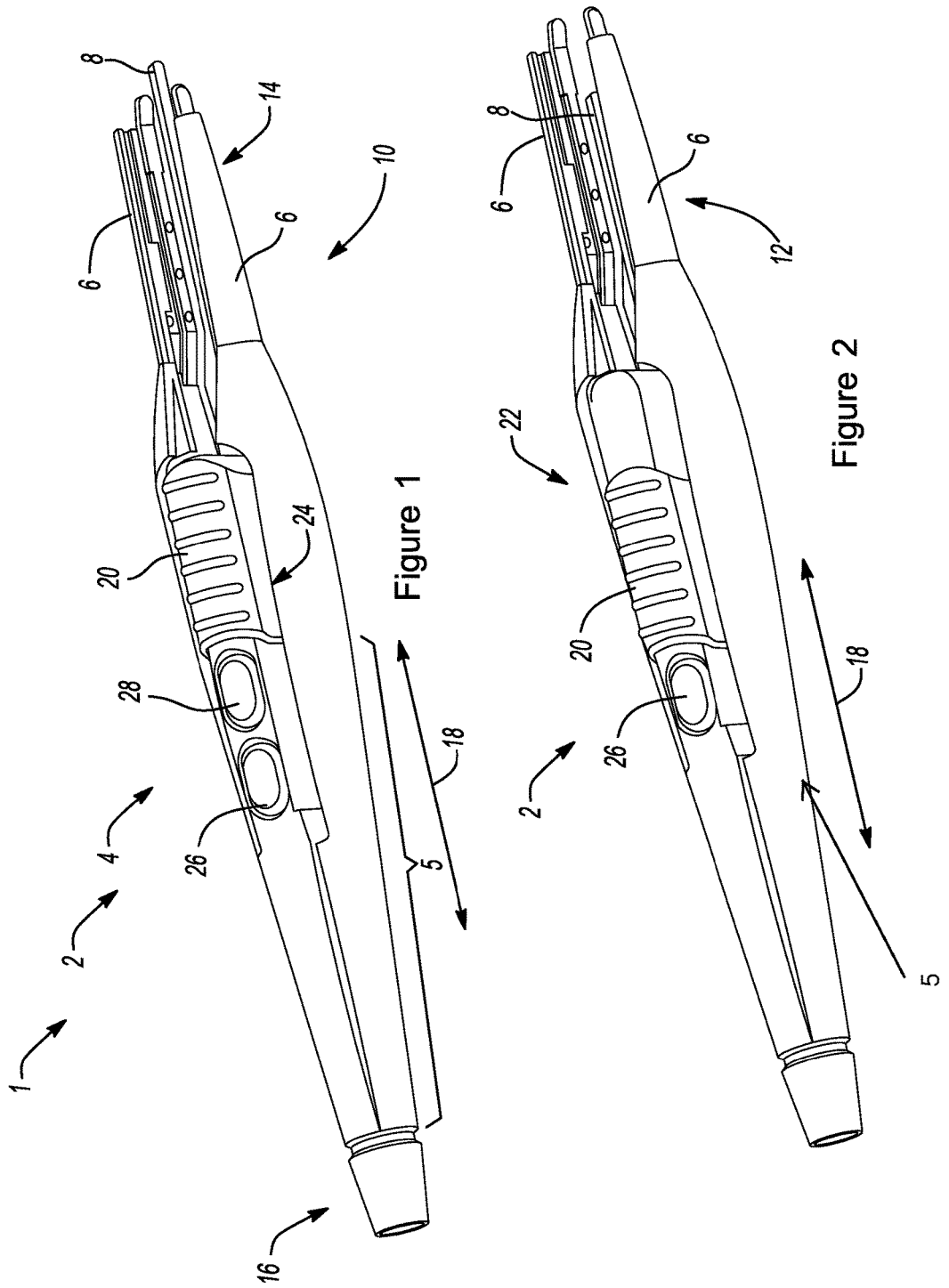

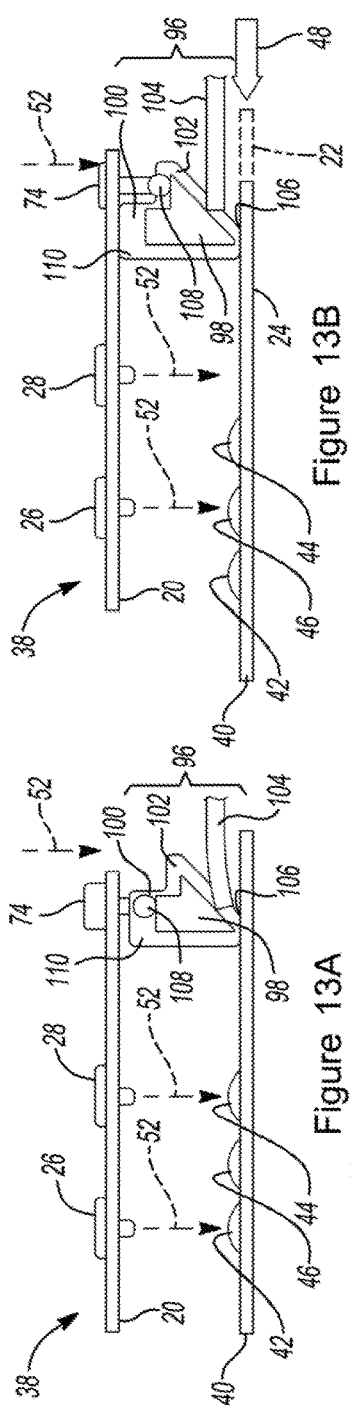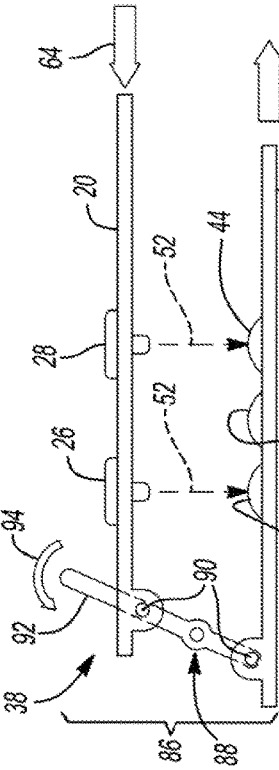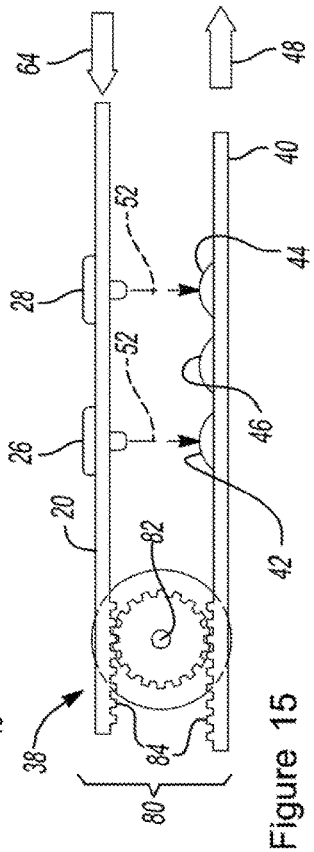

DEVICE WITH MOVABLE BUTTONS OR SWITCHES

FIELD

The present teachings generally relate to devices, more specifically surgical devices that include a circuit board switch and/or buttons that are repositionable between two or more positions so that two or more functional states are enabled.

BACKGROUND

Typically, surgical devices have one functional element, thus if a different function is desired a surgeon will switch devices during a procedure to a device with a different function. However, some devices include a second functional element and each functional element is activated by actuating each individual button. For example, if the surgeon selects a device that has two buttons, one button activates monopolar cut and a second button activates bipolar coagulation, the device can only provide these functions. Thus, if bipolar cutting is desired the surgeon either may use bipolar coagulation for a longer period of time or the monopolar cutting for cutting or the surgeon can switch to a device that provides bipolar cutting. This may result in longer surgery times or a less than optional cut being performed. Further, switching devices in the middle of a procedure may result in the surgeon losing concentration, losing a feature of interest, extending surgery times, or a combination thereof.

Examples of some electrosurgical instruments may be found in U.S. Pat. Nos. 6,110,171; 6,113,596; 6,190,386; 6,358,268; and 7,232,440; and U.S. Patent Application Publication Nos. 2005/0113827; 2005/0187512; 2006/0084973; 2012/0123405; 2014/0276795; and 2014/0276799 all of which are incorporated by reference herein for all purposes. What is needed is a device that easily transforms between a plurality of different electrical states and functions. It would be attractive to have a device that can switch between two or more states and multiple states with a single button. It would be attractive to have a device that mechanically reconfigures states so that the circuitry of the device physically changes position, electrically reconfiguring the device relative to the buttons. The buttons would control the functional output of the device. What is needed is a device that can change states so that each button can provide multiple functions.

SUMMARY

The present teachings meet one or more of the present needs by providing: a surgical device comprising: (a) one or more functional elements, (b) a selector assembly including: (i) one or more activation buttons, (ii) one or more circuit board switches, and (iii) a shuttle in communication with the circuit board or the one or more activation buttons to move the circuit board switches or the activation buttons between at least a first position and a second position so that the circuit board switches or the activation buttons are moveable relative to each other; wherein the one or more functional elements provide a first function when the circuit board switches or the one or more activation buttons are in the first position, and the one or more functional elements provide a second function when the circuit board switches or the one or more activation buttons are in the second position.

Another possible embodiment of the present teachings comprises: an electromechanical device comprising: (a) one or more electrical elements; (b) one or more activation buttons; (c) a first circuit board switch; (d) a second circuit board switch; and (e) a shuttle in communication with the first circuit board switch, the second circuit board switch, the one or more activation buttons, or a combination thereof; wherein the electromechanical device is capable of being switched between a first electrical state and a second electrical state; wherein the shuttle moves between a first position and a second position and assists in converting the electrosurgical device between the first electrical state and the second electrical state; wherein in the first electrical state a first activation button of the one or more activation buttons is aligned with the first circuit board switch so that upon actuation of the first activation button a first electrical function is enabled; wherein the first electrical function is a first therapy current being passed through the one or more electrical elements; wherein in the second electrical state a second activation button of the one or more activation buttons is aligned with the second circuit board switch so that upon actuation of the second activation button a second electrical function is enabled; and wherein the electromechanical device includes one or more of the following: (A) in the first position the second activation button is not aligned with the second circuit board switch so that upon actuation of the second activation button the second electrical function is not enabled; (B) in the second position the first activation button is not aligned with the first circuit board switch so that upon actuation of the first activation button the first electrical function is not enabled by the first activation button; and (C) the first activation button and the second activation button are the same button.

The teachings herein provide: an electromechanical device comprising: (a) one or more electrical elements; (b) one or more activation buttons; (c) one or more circuit board switches; (d) a shuttle in communication with at least one of the one or more circuit board switches, at least one of the one or more activation buttons, or both; wherein the electromechanical device is capable of being switched between a first electrical state and a second electrical state and in the first electrical state a first current is passed through a first electrical element of the one or more electrical elements when a first activation button of the one or more activation buttons is actuated, and in the second electrical state the first current is free from passing through the first electrical element when the first activation button is actuated; wherein the shuttle moves along the electromechanical device between a first position and a second position and assists in converting the electromechanical device between the first electrical state and the second electrical state; wherein the shuttle in the first position is positioned so that the first activation button aligns with a first circuit board switch of the one or more circuit board switches to enable the first electrical state when the first activation button interacts with the first circuit board switch upon actuation of the first activation button; and wherein the shuttle in the second position is positioned so that the first activation button is not aligned with the first circuit board switch, disabling the first electrical state.

The teachings herein provide: a device comprising: (a) activation button; (b) a circuit board; wherein the activation button and the circuit board are movable relative to each other; wherein the movement may be longitudinally (e.g., may move along in the direction of the longitudinal axis of the device); rotationally move around a component of the device (e.g., may follow the contour of the device in a direction substantially perpendicular to the longitudinal axis); may laterally move (e.g., from side to side without following the contour of the device); or a combination thereof.

The teachings herein provide a device that can switch between two or more modes and multiple modes with a single button. The teachings herein provide a device that mechanically changes states so that the circuitry of the device electrically changes state relative to the buttons to change the functional outputs of the device. The teachings provide a device that changes state so that each button can provide multiple functions.

BRIEF DESCRIPTION OF THE DRAWINGS

FIG. 1 is a perspective view of a surgical device in a second state;

FIG. 2 is a perspective view of a surgical device in a first state;

FIG. 13A illustrates a perspective view of the selector assembly with a leaf spring mechanism in a first position;

FIG. 13B illustrates a perspective view of the selector assembly with a leaf spring mechanism in a second position;

FIG. 14 illustrates a perspective view of the selector assembly with a short throw lever assembly;

FIG. 15 illustrates a perspective view of the selector assembly with a rack and pinion assembly.

DETAILED DESCRIPTION

Figure 3:
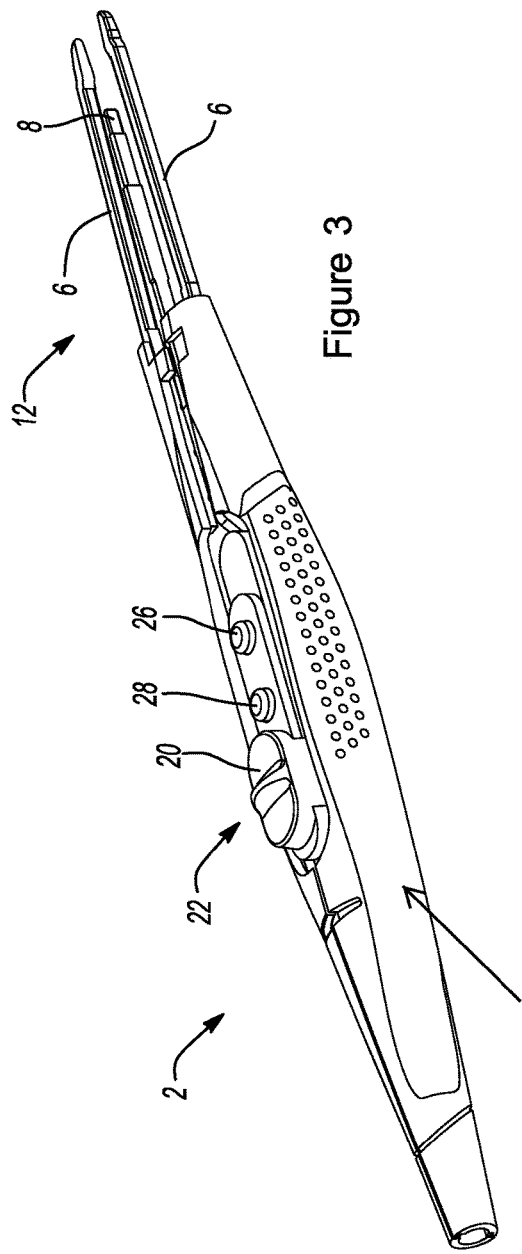
FIG. 3 is a perspective view of a surgical device in a first state.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to a device that is changeable between two or more states. The device may be any device that functions to generate a signal, provide power, or both. The device may transmit a first set of signals in a first state and a second set of signals in a second state. The device may include one or more buttons or one or more keys and the one or more buttons or one or more keys may provide two or more signals depending on the position or state of the keys or buttons (buttons and keys as discussed herein are used interchangeably). The keys, buttons, or both and a circuit board may be movable relative to each other to create different signals so that the device provides different functions. The one or more buttons, one or more keys, or both may be present on a keyboard, a phone, computer, surgical device, or a combination thereof. Preferably, the present teachings relate to buttons on a surgical device. Preferably, the present teachings relate to a surgical device and associated componentry that form an electronic, ultrasonic, or motorized surgical system or a combination thereof.

The surgical device may be a mechanical device, an electromechanical device (e.g., a device with a mechanically moving element and an electrical element), an electrosurgical device, or a combination thereof. The surgical system may be any system that includes one or more of the devices taught herein. Preferably, the surgical system includes at least a surgical device with at least one state (e.g., configuration). The state may be a relative disposition or arrangement of any part of the device that moves relative to another part. For example, the selector assembly moves the buttons relative to the circuit board or vice versa so that the device changes between a first state (or first configuration) and a second state (or second configuration). The surgical system may include one or more bodies as taught herein, one or more ground pads, one or more generators, one or more electrosurgical devices, one or more ultrasonic devices, one or more motorized devices, one or more adjacent body components, or a combination thereof and the teachings herein of each device which are incorporated into the surgical system. The surgical device may be any device that may be used by a surgeon to perform a surgical procedure. The surgical device may function to be switched between two or more configurations, two or more states, or both. For example, the surgical device may be switched between an electrical state, an ultrasonic state, a motorized state, a non-powered state, or a combination thereof. The surgical device may be any device that may be switched between two or more states with one hand so that a user may switch between the states without the need for a second hand, without disrupting the procedure, or both. The surgical device may be any device and/or state that may be used ambidextrously, ambidextrously switched between states, or both. The surgical device may be used to cut, perform hemostasis, coagulate, desiccate, fulgrate, electrocautery, or a combination thereof. The surgical device may perform one or more functions. Preferably, the surgical device performs a plurality of functions. For example, the surgical device may perform a first function, second function, third function, fourth function, or more functions. The surgical device may be any device that includes bipolar capabilities, monopolar capabilities, non-electrosurgical capabilities, ultrasonic capabilities, motorized capabilities (e.g. powered movement to cut, grind, saw, drill or a combination thereof), or a combination thereof. The surgical device may be used in open surgery. The surgical device may be used for non-powered surgical purposes. For example, the surgical device may be used as forceps, tweezers, or both that may be used to grip an object, an organ, a vein, skin, tissue, the like, or a combination thereof. In another example, one or more parts of the device may include a sharp edge and may be used to cut, similar to that of a scalpel. The surgical device may include a handpiece and a generator. The surgical device may have one or more therapy signals that extend between the handpiece and the generator.

The surgical device has a body. The body may function to connect a functional element to a user interface. The body may provide power, signals, or both to the function element. The body and one or more functional elements may be one integral piece or the functional element may be removable from the body. The body may include a power source or be connected to a power source. The body of the device may house the components that are used to make the device functional. The body of the device can be a hand piece. The body of the device can be forceps. The body of the device may be a frame. The body of the device may connect working arms, one or more functional elements, or both. The body of the device may include or be connected to one or more activation buttons, at least one circuit board, a shuttle, the functional element, selector assembly, or a combination thereof.

The selector assembly allows the user to change between a plurality of functions of the surgical device. The selector assembly may function to change between multiple functions for each of the one or more activation buttons. The selector assembly changes the function of the one or more activation buttons by moving the one or more activation buttons, the circuit board, or both. The selector assembly is changeable between two or more positions so that each of the one or more activation buttons provide two or more functions. For example, the surgical device may perform or provide more functions than activation buttons are present on the device (e.g., one button may activate 2 or more, 3 or more, 4 or more, or even 5 or more functions). The selector assembly may longitudinally move along the surgical device (e.g., may move along in the direction of the longitudinal axis of the device (e.g., forceps, motorized device, ultrasonic device)); rotationally move around a component of the surgical device (e.g., the selector assembly may follow the contour of the surgical device in a direction substantially perpendicular to the longitudinal axis); the selector assembly may laterally move (e.g., from side to side without following the contour of the device); or a combination thereof. The longitudinal axis as discussed herein is the dimension with the longest length. The selector assembly may move along or within one or more channels. The selector assembly may be moveable by a sliding action, a leaf spring mechanism, a short throw lever assembly, a rack and pinion assembly, or a combination thereof. The selector assembly may include a portion that is located on a surface of the surgical device and a portion that extends into the surgical device. The selector assembly may change position through the use of a position change button. The position change button may be in communication with a mechanism or assembly that may allow for the selector assembly to move between positions when depressed. The selector assembly may be on the body, removeably attached to a body, movable along the body, or a combination thereof. The selector assembly may include the shuttle, the one or more activation buttons, the circuit board, a position change button, a leaf spring mechanism, a short throw lever assembly, a rack and pinion assembly, or a combination thereof.

The device (e.g., a surgical device) includes a moveable shuttle. The shuttle may be moveable relative to the body of the surgical device. The shuttle may move the device between a plurality of states (e.g., electrical states). For example, the device may be moved from a first state to a second state. The device may be moved between a first state, second state, third state, fourth state, or more states. The shuttle may move along a line or axis of the device; along a surface of the device; pivot as a lever on the device; rotate as a knob on the device; or a combination thereof. The shuttle may move between positions (e.g., first, second, third, or fourth positions) as the shuttle moves along the device. The shuttle may longitudinally move along the surgical device (e.g., may move in the direction of the longitudinal axis of the device); rotationally move around a component of the surgical device (e.g., may follow the contour of the surgical device in a direction substantially perpendicular to the longitudinal axis); the shuttle may laterally move (e.g., from side to side without following the contour of the device); or a combination thereof. The shuttle may move along the longitudinal axis of the surgical device. The shuttle may move in a direction substantially perpendicular to the longitudinal axis (i.e., laterally). The shuttle may move around a rotational axis that is substantially parallel to the longitudinal axis (i.e., rotationally). The shuttle may include one or more of a leaf spring mechanism, a short throw lever assembly, or a rack and pinion assembly that assist in moving the shuttle. The shuttle may be in communication with the one or more activation buttons, the one or more circuit boards, or both. When the shuttle is in communication with the one or more activation buttons, the one or more circuit boards are stationary relative to the body. When the shuttle is in communication with the one or more circuit boards, the one or more activation buttons are stationary relative to the body of the surgical device. When the shuttle is in communication with either the one or more circuit boards or the one or more activation buttons, the one or more activation buttons and the one or more circuit boards may move relative to each other. The shuttle may have two or more positions (e.g., at least a first position and a second position). The shuttle may have a plurality of positions. The shuttle may have a first position, second position, third position, fourth position, or more. The shuttle in one or more of the positions discussed herein may disable one or more of the states herein. The shuttle in a first position may disable a second electrical state, in a second position may disable a first electrical state and/or a third electrical state, or a combination thereof. For example, the shuttle in the second position may be positioned so that the first electrical state is disabled. The shuttle helps convert the surgical device between states based on the shuttle's position. For example, the shuttle in the first position will place the surgical device in the first state and when the shuttle is moved into the second position, the surgical device will be converted to the second state. The shuttle in a first position may align one or more activation buttons with one or more circuit board switches, one or more circuit board switches on a second circuit board, or both. The shuttle in a first position may misalign the one or more activation buttons with the first circuit board switches and align the activation buttons with the second circuit board switches, or vice versa. Alignment as discussed herein is when the button is located so that the button can move into contact with a switch and preferably is when the button can move linearly and substantially perpendicularly to the switch so that the switch is activated upon movement of the button. Misalignment as discussed herein is where the button when activated upon does not contact a switch causing an activation of that switch. The shuttle in the second position may align one or more of the activation buttons with one or more of the circuit board switches, one or more second circuit board switches, or both. The shuttle may be placed in two or more positions so that the one or more activation buttons align with or misalign with the one or more circuit board switches.

The position change button may function to convert the device between two or more positions. The position change button may be in communication with a mechanism or assembly to convert the device between positions (e.g., from a first position to a second position). The position change button when actuated may engage a mechanism or assembly to move the selector assembly from one position to another position by moving the shuttle, the circuit board, the activation buttons, or a combination thereof by converting mechanical potential energy into directional movement. The position change button is located on the exterior of the device. The position change button may include an actuator. The position change button may act upon a leaf spring mechanism, a short throw lever assembly, a rack and pinion assembly, or a combination thereof.

The leaf spring mechanism may convert the device between states (e.g., a first state and a second state). The leaf spring mechanism may include a position change button, an actuator block with a track, a plunger, a leaf spring, or a combination thereof. The actuator block may attach to the circuit board, shuttle, activation buttons, or a combination thereof. The actuator block may have a track. The actuator block track may be on the interior, exterior, or both of the handpiece. The actuator block track may have at least one position. The position change button may be used to convert the leaf spring mechanism between positions. The position change button may include a plunger. The plunger may fit into the track of the actuator block. When the position change button is acted upon, the position change button plunger may move between two or more positions of the actuator block. When the position change button plunger moves, the actuator block may change position so that the leaf spring can push the actuator block, which is connected to the shuttle, the activation buttons, the circuit board, or a combination thereof. The force of the leaf spring expanding may be converted into directional movement, moving the device into another position. When the actuator block is moved from one position to another position, the circuit board, the shuttle, the one or more activation buttons, or combination thereof may be moved relative to each other through the transformation of the potential energy stored in the leaf spring into directional movement.

The short throw lever assembly may be used to convert the device between a plurality of states (e.g., a first state and a second state). The short throw lever assembly when actuated may change the position of the selector assembly from one position to another. The short throw lever assembly may include a lever, a fixed pivot point, one or more moving pivot points, or a combination thereof. The lever may attach to the shuttle, the circuit board, the activation buttons, or a combination thereof at one of the one or more moving pivot points. The lever may pivot about a fixed point. When a force is put onto the lever, the lever may pivot around the fixed point pushing or pulling the circuit board, the shuttle, the activation buttons, or a combination thereof. The short throw lever assembly may move the activation buttons and circuit board into alignment or misalignment. The short throw lever assembly may move the selector assembly by moving the circuit board, the shuttle, the one or more activation buttons, or a combination thereof relative to each other, converting the device from one state to another state.

The rack and pinion assembly may be used to convert the device between a first state and a second state. The rack and pinion assembly may assist in changing the position of the selector assembly from one position to another position. The rack and pinion assembly may include a pinion gear, and one or more rack gears. The rack and pinion assembly may move the selector assembly through rotating a pinion gear in communication with one or more of the rack gears connected with the activation buttons, the shuttle, the circuit board, or a combination thereof. When the assembly is rotated, the teeth of the pinion gear intertwine with the teeth of the rack, which may be connected to the circuit board, the activation buttons, the shuttle, or a combination thereof, moving the circuit board and the activation buttons into alignment or misalignment with one another.

The one or more activation buttons may function to active or deactivate the functional elements. The one or more activation buttons may actuate one or more circuit board switches, align with one or more circuit board switches, or both. The one or more activation buttons may be a plurality of activation buttons. The one or more activation buttons may be a first activation button, a second activation button, a third activation button, a fourth activation button, or more activation buttons. Preferably, each actuation button may actuate one or more circuit board switches so that a plurality of functions may be provided by the surgical device. The one or more activation buttons may contact (e.g., through direct contact or indirect contact) a circuit board switch (e.g., a dome or membrane) to initiate one or more of the functional elements. The one or more activation buttons may move substantially linearly (e.g., perpendicularly to the switches). Each of the one or more activation buttons may provide a different function, control a different functional element, provide multiple functions through the same functional element, or a combination thereof. The one or more activation buttons may be located on the body of the surgical device, on the shuttle, or both. The activation button when depressed actuates a circuit board switch so that one or more of the functional elements of the surgical device are activated. The circuit board switch is actuated when the activation button is depressed, which completes a circuit and powers one or more of the functional elements. There may be more than one activation button present on the surgical device. Preferably there are a plurality of activation buttons. Preferably the one or more of the activation buttons may have a plurality of positions. For example, each of the one or more activation buttons may be moved between a first position and a second position. The one or more activation buttons may be longitudinally moveable along the longitudinal axis of the device, laterally moveable along a secondary dimension of the device (e.g., a direction substantially perpendicular to the longitudinal axis), rotatably moveable about the rotational axis, or a combination thereof. Preferably, the one or more activation buttons will move about the longitudinal axis. The one or more activation buttons may be static. The one or more activation buttons may be static relative to the body, to the shuttle, circuit board, or a combination thereof. The one or more activation buttons may be a rigid element, non-conductive element, or both. The one or more activation buttons may be constrained from motion by guides in the body. The one or more activation buttons when aligned with the circuit board or circuit board switches (i.e., electrosurgical switches) may contact the circuit board or circuit board switches when depressed, activating one or more functional elements.

The circuit board functions to activate or deactivate one or more of the functional elements. The circuit board functions to receive one or more user inputs and control one or more functional elements of the surgical device. There may be more than one circuit board in a surgical device. The circuit board may have surface mounted circuitry, through-hole circuitry, or both. Preferably, the circuit board has surface mounted circuitry. The circuit board may have components mounted or placed onto the surface. For example, all of the circuit componentry, including the circuit board switch, are mounted on the top surface of the circuit board to allow the circuit board to be mounted flat onto the mounting surface of the device. The circuit board may be of a through-hole construction. Through-hole construction fits the components with wire leads into holes in the circuit board. When more than one circuit board is present the circuit boards may be movable relative to each other. For example, one circuit board may be moved over or under another circuit board so that a different function may be activated. One circuit board may be movable and one circuit board may be static. Both circuit boards may be movable. Each of the one or more activation buttons may provide a different function, control a different functional element, provide multiple functions through the same functional element, or a combination thereof. The one or more circuit boards may be located on or within the body of the surgical device, on or within the shuttle, or both. The one or more circuit boards are used to activate a functional element of the surgical device. The one or more circuit boards have at least one switch per circuit board that interact with the one or more activation buttons. The circuit board switches may be surface mounted switches. When the circuit board switch is actuated by the depressed activation button, the circuit board switch closes a circuit of the circuit board and enables the functional element of the surgical device. There may be more than one circuit board present on the surgical device. The surgical device may include a plurality of circuit boards. For example, the surgical device has a first circuit board and a second circuit board. The first circuit board, when activated, enables a first functional element and the second circuit board, when activated, enables a second functional element. The surgical device may have one activation button that moves between the two circuit boards and aligns with the first circuit board when in the first position and the second circuit board in the second position. In the first position, the second circuit is misaligned with the activation button and in the second position, the first circuit board is misaligned with activation button. Preferably the one or more of the circuit boards may have a plurality of position. For example, each of the one or more circuit boards may be moved between a first position and a second position. The one or more circuit boards may be longitudinally moveable along the longitudinal axis of the device, laterally moveable along a secondary dimension of the device (e.g., substantially perpendicular to the longitudinal axis), rotatably moveable about the rotational axis (e.g., an axis that is parallel to the longitudinal axis), or a combination thereof. Preferably, the one or more circuit boards will move about the longitudinal axis. The one or more circuit boards may be static. The one or more circuit boards may be static relative to the body, to the shuttle, the activation buttons, or a combination thereof. There may be more than one circuit board switches on a circuit board. For example, there may be two circuit board switches located on the same circuit board (e.g., a first circuit board switch and a second circuit board switch). For example, both a first circuit board and a second circuit board may include a first circuit board switch and a second circuit board switch. When the first circuit board switch is depressed, a first function is performed and when the second circuit board switch is depressed, a second function is performed. The circuit board may include one or more switches.

The circuit board switches enable the surgical device to activate functional elements through interacting with the circuit board and the one or more activation buttons. Each of the circuit boards may include one or more switches and preferably a plurality of switches. The one or more switches may be a first switch, a second switch, a third switch, a fourth switch, a fifth switch, or more switches. The device may include the same number of switches as buttons. For example, the device may include two buttons and two switches. The device may include a different number of buttons and switches. For example, the device may include three switches and one button. In another example the device may include two buttons and three switches. The one or more circuit board switches may be flat, convex, concave, a dome switch, a membrane switch, an electrical switch, a capacitive sensor, a pressure sensor, or a combination thereof. Preferably, the one or more circuit board switches may be a dome switch. The one or more circuit board switches interact with the one or more activation buttons when the one or more activation buttons are aligned with the circuit board switches such that when the one or more activation buttons are depressed, the buttons make contact with and engage the one or more circuit board switches to complete the circuit, enabling a functional element of the surgical device. The circuit board switches may be activated without being contacted. For example, depression of an activation button may create a field that triggers the circuit board switch so that a function is activated. The one or more circuit board switches and the one or more activation buttons are brought into alignment by changing the position of the selector assembly.

The state (e.g., electrical state or mechanical state) of the surgical device is changeable so that a functional element is activated. The surgical device has at least two states. Each of the states provide one or more different functions. For example, the first state is a forceps and provides a bipolar therapy current and a second state is a probe that may provide cutting and provides a monopolar therapy current. The surgical device creates a first state when the selector assembly is in the first position. When the selector assembly is in the first position, at least one circuit board switch is aligned with at least one of the activation buttons so that when the activation button is engaged, the activation button contacts the circuit board switch on the circuit board, completing the circuit and enabling a first function.

The second state changes the surgical device (e.g., mechanically or electrically) into a secondary form to allow a second element of the surgical device to be used. The second state is created when the selector assembly is in the second position. In the second state the selector assembly is advanced to the second position where the selector assembly moves either the one or more circuit boards or the one or more activation buttons. When the circuit boards or activation buttons are moved, the previously enabled function is no longer accessible due to the misalignment or realignment of the activation buttons and the circuit board switches. In the second state one or more of the activation buttons may be misaligned with one or more of the circuit board switches so that the activation button that is misaligned is effectively disabled. In the second state, the selector assembly is in the second position so that the activation button and the circuit board switch on the circuit board may be misaligned, so when the activation button is depressed, the button does not contact the circuit board switch and does not enable one or more of the functional elements. The second state of the surgical device may realign one of the activation buttons with one of the circuit board switches so that a functional element is activated, which is different than the functional element activated in the first state. In the second state the shuttle is in the second position so that at least one of the activation buttons are aligned with another circuit board switch, differing from the alignment in the first state so when the activation button is depressed, the button makes contact with the circuit board switch, enabling a second functional element of the surgical device. For example, if the first functional element produces a therapy current, the second functional element may be a different therapy current. The second state of the surgical device may be a non-powered element.

The one or more functional elements are an integral part of the surgical device or a part that may be added to the surgical device so that the surgical device may be used to perform a surgical procedure. The surgical device has at least one functional element. The functional element may be actuated when the circuit is completed by depressing the one or more activation buttons. Preferably, the surgical device has more than one functional element. For example, the surgical device may be electrosurgical forceps where in the first state the electrosurgical forceps produce a therapy current and in the second state the surgical device would function as non-electrical forceps. Preferably, the surgical device has a plurality of functional elements (e.g., three or more, four or more, or even five or more). The functional elements may be electrical, motorized, ultrasonic, mechanical, or a combination thereof.

When the functional elements are electrical elements the functional elements use electricity to perform one or more portions of a surgical procedure. Electrical elements are functional elements that use electricity to operate. The electrical element may be an electrode, an electrical motor, an ultrasonic transducer, or a combination thereof. The first electrical element may be a motor and the second electrical element may be an electrode. The second electrical element may be an electrode, a second therapy current, a motor, an ultrasonic transducer, or a combination thereof. Preferably, the second electrical element is a second therapy current that passes through at least the second electrical element. The motor may be operated when an activation button is in a first position and the electrode may be activated when the activation button is in a second position. The surgical device may have at least one electrical element. The surgical device may have at least two electrical elements. The surgical device may have a plurality of electrical elements.

The electrical functional element of the surgical device may include one or more electrodes. Electrodes conduct electricity through the surgical device upon activation. Electrodes may conduct therapy currents. A therapy current may be a monopolar current, bipolar current, or a combination thereof. The therapy current may be used to cut, cauterize, coagulate, or a combination thereof during a surgery. The electrodes may conduct a therapy current that is used to actuate a motor.

The functional element of the surgical device may be a motor. A motor functions to move a component of the surgical device. The motor may be electrically powered, pneumatically powered, hydraulically powered, or a combination thereof. The motor may be used to cut, grind, saw, drill, or a combination thereof. For example, the motorized functional element of the surgical device may be a debrider, which has a stationary outer blade and rotating inner blade or the motorized functional element may be a second functional element such as irrigation or suction. In the first functional state, the debrider may be actuated and in the second functional state the irrigation or suction element may be actuated by an opening of a solenoid powered valve impinging on a fluid line. For example, the device in a first state may actuate a debrider function to cut a targeted area, and the device in a second state may actuate a vacuum source to remove debris and liquid from a targeted area, and in a third state may actuate an irrigation source to provide saline solution to a targeted area. The vacuum and irrigation may be obtained from a preexisting source and may be actuated by the activation of a solenoid. In another example, the device in a first state activates the debrider function and the device in a second state activates a bipolar coagulation function without activating the debrider motor.

The functional element of the surgical device may be an ultrasonic component. The ultrasonic functional element may be used to identify a targeted area, cut, coagulate, or a combination thereof. It is preferred that the ultrasonic element cuts and coagulates by converting the electrical energy to mechanical vibration that is applied to tissue. Ultrasonic capabilities can be combined with a monopolar function, a bipolar function, or both. For example, the device in a first state may be actuated to produce ultrasonic energy to cut a targeted area, and the device in a second state may actuate a bipolar therapy current to coagulate a targeted area. In a further example, the device in the first state sends ultrasonic energy to a targeted area, and in the second state sends both ultrasonic and bipolar energy to a targeted area to simultaneously cut and coagulate.

The functional element of the surgical device may be mechanical device. A mechanical functional device is substantially free of electricity or any other power source. The mechanical element may be using the surgical device to cut, grip, probe, saw, strike, or a combination thereof.

The surgical device may be a combination device. A combination device incorporates two or more structural elements into a single device to make a tool that is capable of performing multiple functions without switching handsets.

FIG. 1 illustrates a perspective view of one example of a surgical device 1 that is shown as an electrosurgical device 2. The electrosurgical device 2 is shown as forceps 4 having a body 5 with a distal end 14 and a proximal end 16. The distal end 14 includes a pair of working arms 6 with a blade electrode 8 there between. The blade electrode 8 is advanced forward into a first state 10 by the shuttle 20 being moved forward into a second position 24 (i.e. along the longitudinal axis 18). In the second position 24 both the first activation button 26 and the second activation button 28 are shown.

FIG. 2 illustrates a perspective view of the electrosurgical device 2 with the shuttle 20 (along the longitudinal axis 18) in the first position 22 and the blade electrode 8 in the second state 12 so that the blade electrode 8 is retracted between the pair of working arms 6. When the shuttle 20 is in the first position 22 the first activation button 26 is exposed.

FIG. 3 illustrates a perspective view of an electrosurgical device 2 with a shuttle 20 in the first position 22. In the first position 22 the first activation button 26 and second activation button 28 are exposed and the blade electrode 8 is retracted between the working arms 6 so that a second state 12 is created.

Figure 4:
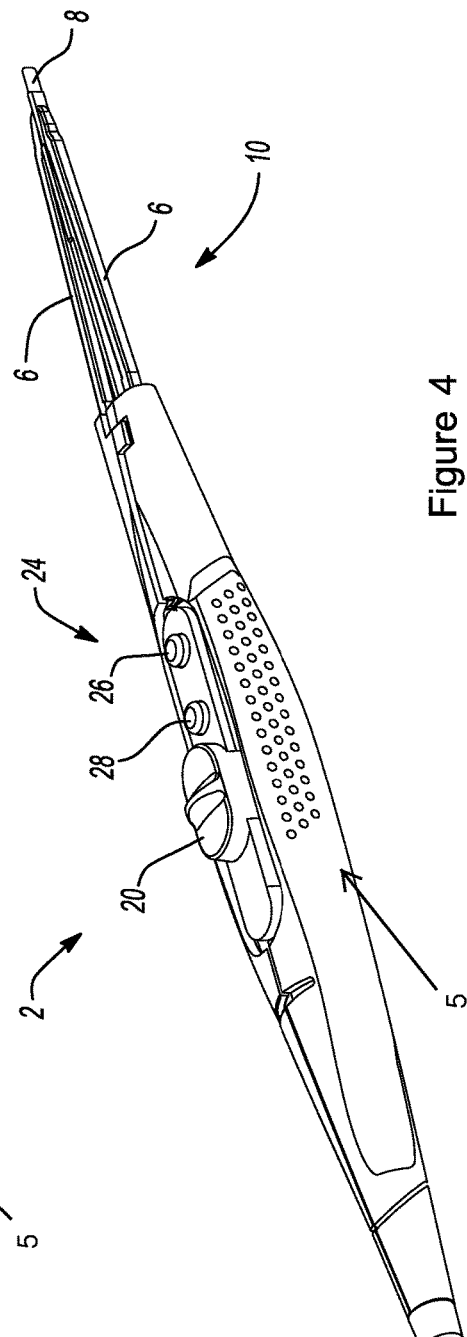
FIG. 4 is a perspective view of a surgical device in a second state.

FIG. 4 illustrates a perspective view of an electrosurgical device 2 with the shuttle 20 in the second position 24. As shown, both a first activation button 26 and a second activation button 28 are exposed for providing power to the blade electrode 8. The blade electrode 8 is advanced forward into the first state 10 so that the blade electrode 8 extends beyond the pair of opposing working arms 6.

Figure 5:
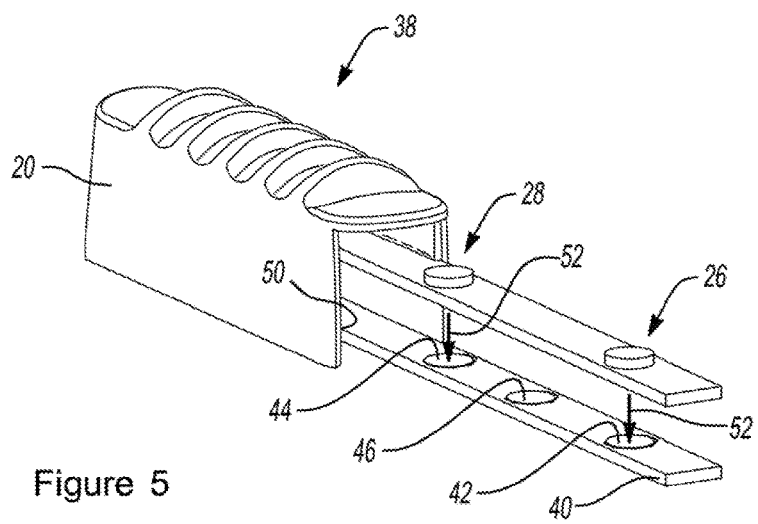
FIG. 5 is a perspective view of a selector assembly in a first position where the circuit board is moveable relative to the activation buttons.

FIG. 5 illustrates a selector assembly 38 including a shuttle 20 connected to a circuit board 40 at a connection region 50. The printed circuit board 40 includes a plurality of switches (e.g., a first circuit board switch 42 and a second circuit board switch 44). As illustrated a first activation button 26 is aligned with a first electrosurgical switch 42 and a second activation button 28 is aligned with a second electrosurgical switch 44 so that when the first activation button 26 or second activation button 28 are actuated in the direction 52 contact is created with the first electrosurgical switch 42 and the second electrosurgical switch 44 respectively. The third electrosurgical switch 46 is misaligned with the activation buttons.

Figure 6:
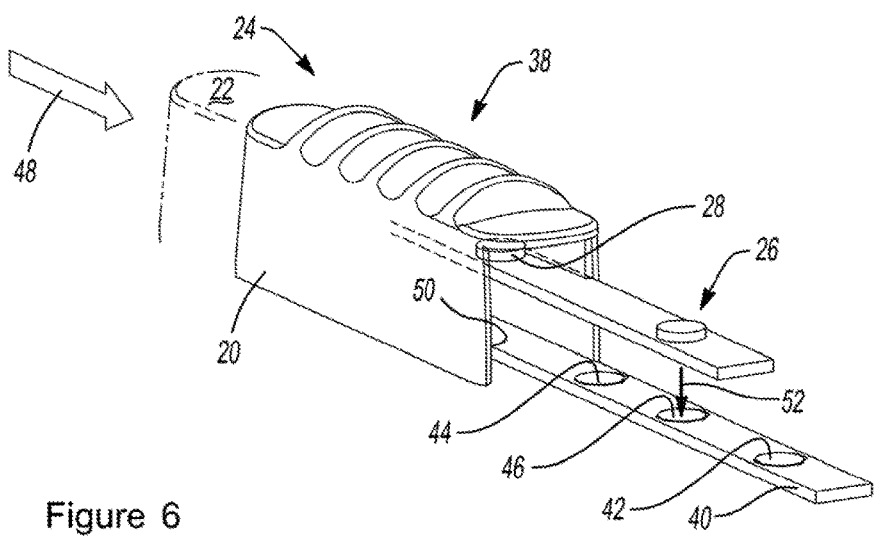
FIG. 6 is a perspective view of a selector assembly in a second position where the circuit board is moveable relative to the activation buttons.

FIG. 6 illustrates the selector assembly 38 including shuttle 20 and circuit board 40 that are moved in the direction 48 so that the third circuit board switch 46 is aligned with the first activation button 26 so that when the first activation button 26 is moved in the direction 52 into contact with the third circuit board switch 46 an electrical mode is activated. The shuttle 20 and the circuit board 40 are connected together at a connection region 50 and move in unison. When the shuttle 20 is moved from position one 22 into the second position 24 the second activation button 28 is covered and misaligned so the activation button 28, if actuated, would not contact any circuit board switch. The first circuit board 42 switch and second circuit board switch 44 are misaligned with all of the activation buttons 26, 28. The blade electrode (not shown) is retracted.

Figure 7:
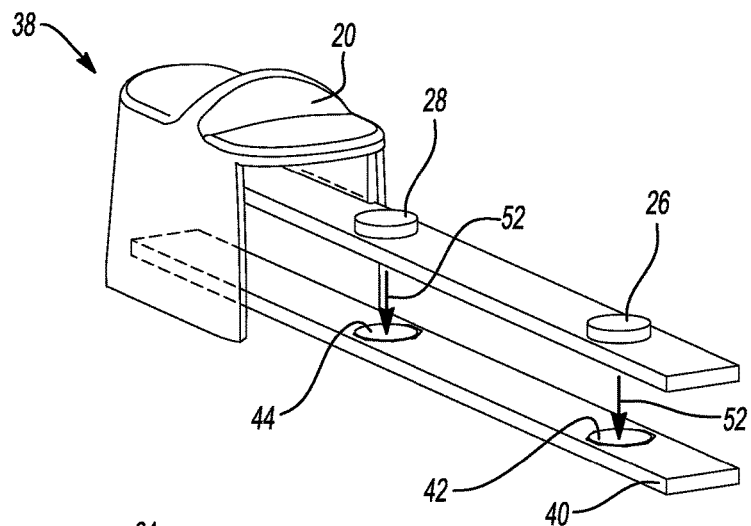
FIG. 7 is a perspective view of a selector assembly in a first position where the activation buttons are moveable relative to the circuit board.

FIG. 7 illustrates a selector assembly 38 including shuttle 20, and activation buttons 26, 28. The circuit board 40 includes a plurality of switches (e.g., a first electrosurgical switch 42 and a second electrosurgical switch 44). As illustrated a first activation button 26 is aligned with a first electrosurgical switch 42 and a second activation button 28 is aligned with a second electrosurgical switch 44 so that when the first activation button 26 or second activation button 28 are actuated in the direction 52 contact is created with the first electrosurgical switch 42 and the second electrosurgical switch 44 respectively.

Figure 8:
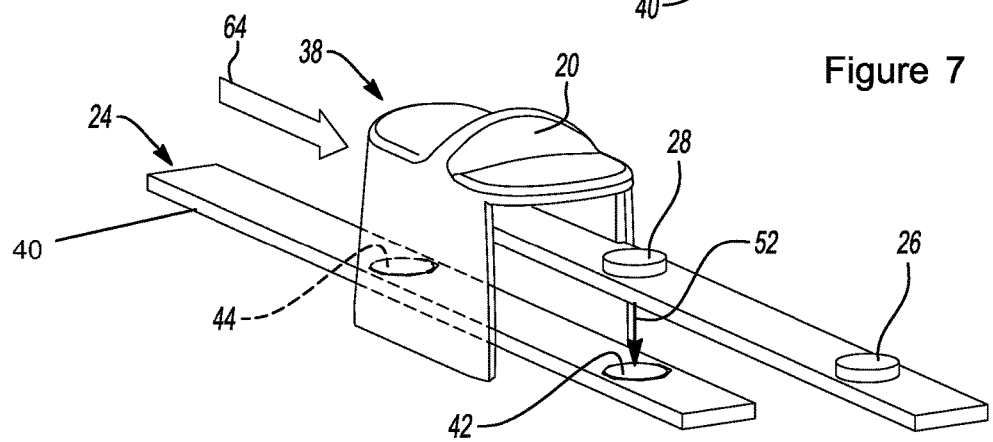
FIG. 8 is a perspective view of a selector assembly in a second position where the activation buttons are moveable relative to the circuit board.

FIG. 8 illustrates the selector assembly 38 including shuttle 20 and activation buttons 26, 28 are moved in the direction 64 so that the second activation button 28 is aligned with the first electrosurgical switch 42 so that when the second activation button 28 is moved in the direction 52 into contact with the first activation switch 42 an electrical mode is activated. The first activation button 26 is positioned so that it does not interact with the circuit board switches 42, 44. The second circuit 44 board switch is positioned so it cannot be actuated by an activation button 26, 28. The shuttle 20 includes the activation buttons 26, 28 and move in unison in direction 64 to place the device in position two 24.

Figure 9:
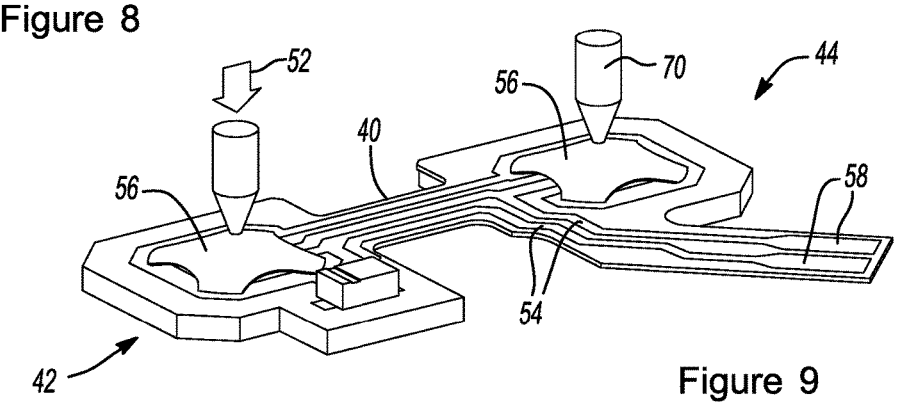
FIG. 9 illustrates a perspective view of circuit switches.

FIG. 9 illustrates a first electrosurgical switch 42 and a second electrosurgical switch 44 with a circuit board 40 including traces 54 that have a terminal 58 region. A dome 56 is in contact with and extends over the traces 54 so that when an activation device 70 actuates the dome 56 in direction 52 a signal is sent.

Figure 10:
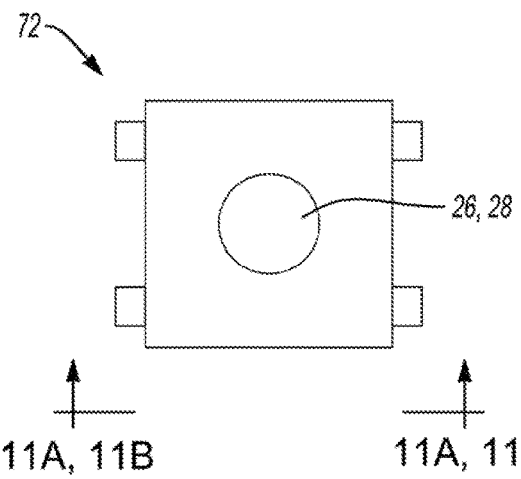
FIG. 10 illustrates a top view of a switch.

FIG. 10 illustrates a top view of a switch 72. The switch 72 includes a button that can be a first activation button 26 or a second activation button 28.

Figure 11A:
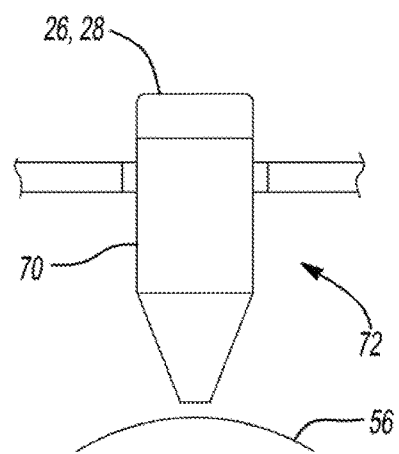
FIG. 11A illustrates a view of the first or second activation button and the circuit board switch in a non-activation position.

FIG. 11A illustrates a side view of the switch 72 during an off position. In the off position the dome 56 is extended upward towards the activation device 70 that is connected to the first activation button 26/second activation button 28.

Figure 11B:
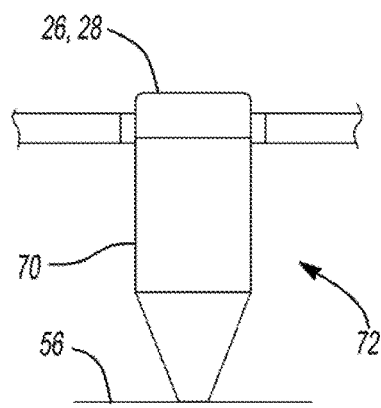
FIG. 11B illustrates the first or second activation button depressing the circuit board switch.

FIG. 11B illustrates the switch 72 in an activation position. In the activation position, the dome 56 is actuated by the activation device 70 being pushed against the dome by the first activation button 26/second activation button 28.

Figure 12A:
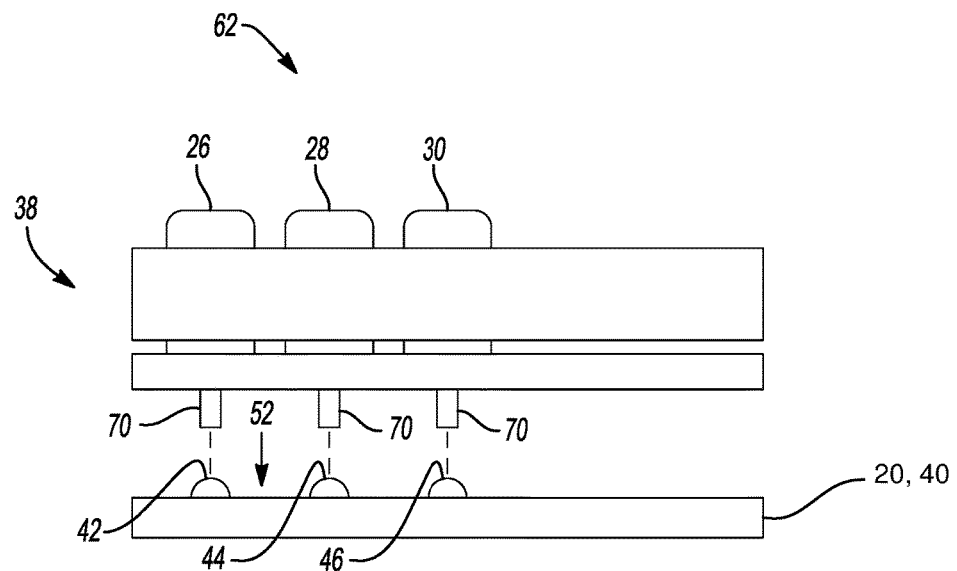
FIG. 12A illustrates a perspective view of the device as a keyboard in a first position.

FIG. 12A illustrates the selector assembly 38 as a keyboard 62 with multiple activation buttons 26, 28, 30 aligned with multiple circuit board switches 42, 44, 46 located on the circuit board 40, so when one or more of the activation buttons 26, 28, 30 are depressed in direction 52, one or more of the circuit board switches 42, 44, 46 are actuated, respectively. The buttons 26, 28, 30 are connected to actuation devices 70, so when the buttons 26, 28, 30 are depressed in the 52 direction, the actuating device 70 depress the respective circuit board switch 42, 44, 46.

Figure 12B:
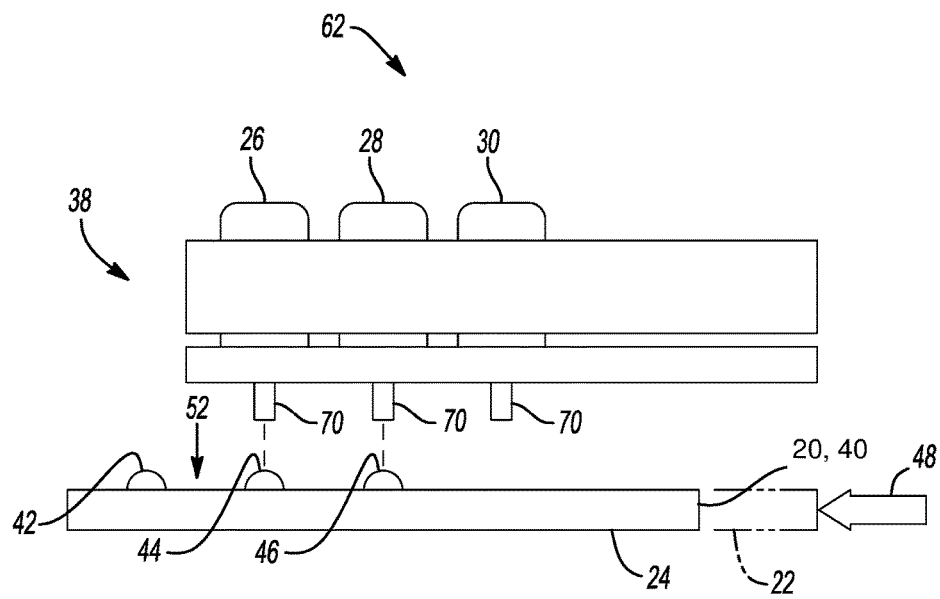
FIG. 12B illustrates a perspective view of the device as a keyboard in a second position.

FIG. 12B illustrates a selector assembly 38, which is shown as a keyboard 62. The circuit board 40 of the keyboard 62 is shown moving in the 48 direction from a first position 22 to a second position 24. In the second position 24 alignment of the circuit board switches 42, 44, 46 are changed relative to the first position 22. As shown activation button 26 is aligned with circuit board switch 44, activation button 28 is aligned with circuit board switch 46 and activation button 30 is misaligned (i.e., does not align with a circuit board switch). So when the activation buttons 26 and 28 are depressed in the 52 direction, the actuation device 70 will contact the circuit board switches 44 and 46. Similarly, Circuit board switch 42 is misaligned and does not align with an activation button and thus this functionality is effectively unactuatable.

FIG. 13A illustrates the selector assembly 38 in position one. The selector assembly 38 is connected to the circuit board 40 through a leaf spring mechanism 96. In position one, the activation buttons 26, 28 are carried on the shuttle 20 and are aligned with the circuit board switches 42, 44. When activation buttons 26, 28 are depressed in the direction 52, the activation button 26, 28 will contact circuit board switches 42, 44, respectively. No activation buttons are aligned with circuit board switch 46. The selector assembly includes a position change button 74 which is in communication with the leaf spring mechanism 96. The leaf spring mechanism 96 includes an actuator block 98 with a track 110, a plunger 108, and a leaf spring 104. The actuator block 98 attaches to the circuit board at region 106. The track 110 of the actuator block 98 has a top position 100 and a side position 102. The plunger 108 is connected to the position change button 74 and fits into the positions of the actuator block 100, 102 so when the position change button 74 is acted upon in direction 52, the plunger 108 moves from the top position 100 to the side position 102. When the plunger 108 moves, the leaf spring 104 can push the actuator block 98, which is connected to the circuit board 40 at 106, converting the device into position two. When the actuator block is moved from position one to position two, the circuit board 40 is moved relative to the activation buttons 26, 28. To move the device back to position one, the position change button can be actuated, causing the plunger to move about the track of the actuator block clockwise so that the plunger returns to position one.

FIG. 13B illustrates the selector assembly 38 in position two 24. The selector assembly 38 is connected to the circuit board 40 through a leaf spring mechanism 96. The leaf spring mechanism 96 moves the circuit board 40 in direction 48, where the shuttle 20 holds the activation button 26 to align with the circuit board switch 46. The second activation button 28 is misaligned with all of the circuit board switches 42, 44, 46. The first circuit board switch 42 and second circuit board switch 44 are not aligned with any of the activation buttons. When activation button 26 is depressed in the direction 52, it will contact the circuit board switch 46. The leaf spring assembly 96 converts the device from position one 22 to position two 24 through actuating the position change button 74 in the direction 52. The position change button depresses the plunger 108 causing the leaf spring mechanism 96 to relieve tension on the leaf spring 104 which expands and moves the circuit board 40 laterally by pushing the actuator block 98, which is connected to the circuit board 40 at 106, placing the device in the second position 24. When the position change button 74 is depressed, the plunger 108 moves along the track 110 of the actuator block 98 from the top position 100 to the side position 102. The circuit board 40 moves relative to the activation buttons 26, 28. The activation buttons 26, 28 are stationary relative the circuit board 40.

FIG. 14 illustrates the selector assembly 38 connected to the circuit board 40 through a short throw lever assembly 86 where the shuttle 20 holds the activation buttons 26, 28 aligns with the circuit board switches 42, 44 so that when the activation buttons 26, 28 are depressed in the direction 52, the activation buttons 26, 28 will contact the circuit board switches 42, 44 respectively. In this position, the third circuit board switch 46 is not aligned with either of the activation buttons 26, 28. The short throw lever assembly 86 includes a lever 92, a fixed pivot point 88 that the lever rotates about, and moving pivot points 90 at the circuit board and the shuttle, respectively. The short throw lever assembly 86 converts the device between positions when moved in the 94 direction by laterally moving the shuttle 20 holding the activation buttons 26 and 28 in the 64 direction and the circuit board 40 in the 48 direction. The shuttle 20 and the circuit board 40 are connected by the lever 92 at moving pivot points 90, so when the short throw lever assembly 86 is acted upon, the lever 92 pivots about the fixed point 88, moving the shuttle 20, which holds the activation buttons 26 and 28, and the circuit board 40 into aligned or misaligned.

FIG. 15 illustrates the selector assembly 38 is connected to the circuit board 40 and shuttle 20 through a rack and pinion assembly 80. The rack and pinion assembly 80 helps convert the device between a first position and a second position by allowing the shuttle 20, carrying the activation buttons 26 and 28, to move relative to the circuit board 40. The rack and pinion assembly 80 includes a pinion gear 82 and a pair of rack gears 84, each attached to the circuit board 40 and the shuttle 20. As the pinion gear 82 rotates, the rack gears 84 laterally move the shuttle 20 in the 64 direction and circuit board 40 in the 48 direction placing the device into a second position, aligning or misaligning the activation buttons 26, 28 with the circuit board switches 42, 44, 46. In the position shown, the activation buttons 26 and 28 are aligned with circuit board switches 42 and 44, so when the activation buttons are depressed in the 52 direction, activation button 26 will contact circuit board switch 42 and activation button 28 will contact circuit board switch 44. Circuit board switch 46 is not aligned with any activation buttons. A rack and pinion converts rotational movement to longitudinal movement or lateral movement.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:
1. A surgical device comprising:
   a. one or more functional elements, and
   b. a selector assembly including:
      i. one or more activation buttons,
      ii. one or more circuit boards with one or more circuit board switches, and
      iii. a shuttle in communication with the one or more activation buttons to move the one or more activation buttons between at least a first position and a second position so that the one or more activation buttons are moveable relative to the one or more circuit board switches;
wherein the one or more functional elements provide a first function when the one or more activation buttons are in the first position, and the one or more functional elements provide a second function when the one or more activation buttons are in the second position;
wherein the surgical device is capable of being switched between a first electrical state and a second electrical state by moving the shuttle between the first position and the second position;
wherein in the first electrical state a first of the one or more activation buttons is aligned with a first of the one or more circuit board switches so that the one or more functional elements are operable to provide the first function when the first of the one or more activation buttons is selectively actuated; and
wherein in the second electrical state the first of the one or more activation buttons is misaligned with the first of the one or more circuit board switches so that the one or more functional elements are not operable to provide the first function when the first of the one or more activation buttons is selectively activated.

2. The surgical device of claim 1, wherein the second function is free of an electrical element.

3. The surgical device of claim 1, wherein at least one of the one or more functional elements is an electrode, a motor, or an ultrasonic transducer.

4. The surgical device of claim 1, wherein in the second electrical state a second of the one or more activation buttons is aligned with a second of the one or more circuit board switches so that the one or more functional elements are operable to provide the second function when the second of the one or more activation buttons is selectively actuated; and wherein in the first electrical state the second of the one or more activation buttons is misaligned with the second of the one or more circuit board switches so that the one or more functional elements are not operable to provide the second function when the second of the one or more activation buttons is selectively actuated.

5. The surgical device of claim 1, wherein the surgical device is capable of being switched between a first electrical state and a second electrical state by moving the shuttle between the first position and the second position;
wherein in the first electrical state a first of the one or more activation buttons is aligned with a first of the one or more circuit board switches so that the one or more functional elements are operable to provide the first function when the first of the one or more activation buttons is selectively actuated; and
wherein in the second electrical state the first of the one or more activation buttons is aligned with a second of the one or more circuit board switches so that the one or more functional elements are operable to provide the second function when the first of the one or more activation buttons is selectively actuated.

6. The surgical device of claim 1, wherein the surgical device further comprises a body and the shuttle moves relative to the body.

7. The surgical device of claim 6, wherein the selector assembly further includes a short throw lever assembly including a lever, a fixed pivot point that the lever rotates about, a first moving pivot on the shuttle, and a second moving pivot on the one or more circuit boards;
wherein the lever connects to the shuttle, carrying the one or more activation buttons, at the first moving pivot, with the one or more circuit boards at the second moving pivot;
wherein the short throw lever assembly changes between the first position and the second position by moving the shuttle from the first position to the second position, moving the one or more circuit boards in an opposite direction of the shuttle.

8. The surgical device of claim 6, wherein the selector assembly further includes a rack and pinion assembly including a pinion gear, a first rack gear on the shuttle, and a second rack gear on the one or more circuit boards;
wherein the pinion gear connects the shuttle, carrying the one or more activation buttons, at the first rack gear with the one or more circuit boards at the second rack gear;
wherein the shuttle moves between the first position and the second position by rotating the pinion gear moving the one or more circuit boards in an opposite direction of the shuttle.

9. An electromechanical device comprising:
a. one or more electrical elements;
b. one or more activation buttons;
c. at least one circuit board with a first circuit board switch and a second circuit board switch; and
d. a shuttle in communication with the one or more activation buttons;
wherein the electromechanical device is capable of being switched between a first electrical state and a second electrical state;
wherein the shuttle moves between a first position and a second position and assists in converting the electromechanical device between the first electrical state and the second electrical state;
wherein in the first electrical state, a first activation button of the one or more activation buttons is aligned with the first circuit board switch so that upon actuation of the first activation button a first electrical function is enabled;
wherein the first electrical function is a first therapy current being passed through the one or more electrical elements;
wherein in the second electrical state a second activation button of the one or more activation buttons is aligned with the second circuit board switch so that upon actuation of the second activation button a second electrical function is enabled; and
wherein the electromechanical device includes one or more of the following:
(A) in the first position, the second activation button is not aligned with the second circuit board switch so that upon actuation of the second activation button the second electrical function is not enabled;
(B) in the second position, the first activation button is not aligned with the first circuit board switch so that upon actuation of the first activation button the first electrical function is not enabled by the first activation button.

10. The electromechanical device of claim 9, wherein the one or more electrical elements includes a first electric element that is an electric motor, an electrode or an ultrasonic transducer.

11. The electromechanical device of claim 9, wherein the second electrical function is a second therapy current passing through the first electrical element.

12. The electromechanical device of claim 9, wherein the first activation button and the second activation button are the same button.

13. The electromechanical device of claim 9, wherein the one or more electrical elements includes a second electrical element and the second electrical function is a second therapy current passing through at least the second electrical element.

14. The electromechanical device of claim 13, wherein the first activation button is aligned with the first circuit board switch, directing a first therapy current through the first electrical element and the second activation button is free of enabling any of the one or more electrical elements while the shuttle is in the first position, and when the shuttle is in the second position, the second activation button is aligned with the second circuit board switch so that the second therapy current is directed to the second electrical element, while the first button is free of enabling any of the one or more electrical element.

15. An electromechanical device comprising:
  a. one or more electrical elements;
  b. one or more activation buttons;
  c. one or more circuit boards with one or more circuit board switches;
  d. a shuttle in communication with at least one of the one or more activation buttons;
  wherein the electromechanical device is capable of being switched between a first electrical state and a second electrical state and in the first electrical state a first current is passed through a first electrical element of the one or more electrical elements when a first activation button of the one or more activation buttons is actuated, and in the second electrical state the first current is free from passing through the first electrical element when the first activation button is actuated;
  wherein the shuttle moves along the electromechanical device between a first position and a second position and assists in converting the electromechanical device between the first electrical state and the second electrical state;
  wherein the shuttle in the first position is positioned so that the first activation button aligns with a first circuit board switch of the one or more circuit board switches to enable the first electrical state when the first activation button interacts with the first circuit board switch upon actuation of the first activation button; and
  wherein the shuttle in the second position is positioned so that the first activation button is not aligned with the first circuit board switch, disabling the first electrical state.

16. The electromechanical device of claim 15, wherein at least one of the one or more activation buttons are located on a keyboard.

17. The electromechanical device of claim 15, further comprising a second circuit board switch so that when the shuttle is in the second position, one of the one or more activation buttons is aligned with the second circuit board switch to enable a second electrical state and in the second electrical state a second current is passed through one of the one or more electrical elements when the one of the one or more activation buttons are actuated.

18. The electromechanical device of claim 17, wherein when the shuttle is in the first position, the second circuit board switch is not aligned with the one or more activation buttons, disabling the second electrical state.

19. The electromechanical device of claim 17, wherein the electromechanical device includes a second electrical element and in the second electrical state the second current is a current that passes through the second one of the one or more electrical elements.

* * * * *